(12) United States Patent
Asmatulu et al.

(10) Patent No.: US 9,782,342 B2
(45) Date of Patent: Oct. 10, 2017

(54) COMPOSITE MAGNETIC NANOPARTICLE DRUG DELIVERY SYSTEM

(75) Inventors: Ramazan Asmatulu, Wichita, KS (US); Heath Misak, Wichita, KS (US); Shang-You Yang, Wichita, KS (US); Paul Wooley, Wichita, KS (US)

(73) Assignee: Wichita State University, Wichita, KS (US)

( * ) Notice: Subject to any disclaimer, the term of this patent is extended or adjusted under 35 U.S.C. 154(b) by 0 days.

(21) Appl. No.: 13/271,172

(22) Filed: Oct. 11, 2011

(65) Prior Publication Data

US 2012/0265001 A1  Oct. 18, 2012

Related U.S. Application Data

(60) Provisional application No. 61/392,018, filed on Oct. 11, 2010.

(51) Int. Cl.
| | | |
|---|---|---|
| *A61M 37/00* | (2006.01) | |
| *A61K 9/00* | (2006.01) | |
| *A61K 33/24* | (2006.01) | |
| *A61K 9/50* | (2006.01) | |

(52) U.S. Cl.
CPC .......... *A61K 9/0009* (2013.01); *A61K 9/5031* (2013.01); *A61K 9/5094* (2013.01)

(58) Field of Classification Search
USPC .................................... 600/12; 424/600, 649
See application file for complete search history.

(56) References Cited

U.S. PATENT DOCUMENTS

| | | | |
|---|---|---|---|
| 5,565,215 A | 10/1996 | Gref | |
| 2006/0041182 A1 | 2/2006 | Forbes | |
| 2007/0264199 A1* | 11/2007 | Labhasetwar et al. | ...... 424/9.32 |
| 2008/0160095 A1 | 7/2008 | Desai | |
| 2009/0291139 A1* | 11/2009 | Trieu | ............... G01N 33/57407 514/1.1 |

OTHER PUBLICATIONS

Guo et al. (Cell-penetrating albumin conjugates for enhanced doxorubicin deliver, Polymer Chemistry, 2013, 4, 4584).*
Lee, et al. Effect of formulation and processing variables on the characteristics of microspheres for water-soluble drugs prepared by w/o/o double emulsion solvent diffusion method. International Journal of Pharmaceutics, 2000, vol. 196, pp. 75-83.

* cited by examiner

*Primary Examiner* — Adam C Milligan
(74) *Attorney, Agent, or Firm* — Tracey S. Truitt

(57) ABSTRACT

A composite magnetic nanoparticle drug delivery system provides targeted controlled release chemotherapies for cancerous tumors and inflammatory diseases. The magnetic nanoparticle includes a biocompatible and biodegradable polymer, a magnetic nanoparticle, the biological targeting agent human serum albumin, and a therapeutic pharmaceutical composition. The composite nanoparticles are prepared by oil-in-oil emulsion/solvent evaporation and high shear mixing. An externally applied magnetic field draws the magnetic nanoparticles to affected areas. The biological targeting agent draws the nanoparticles into the affected tissues. Polymer degradation provides controlled time release delivery of the pharmaceutical agent.

24 Claims, 12 Drawing Sheets
(9 of 12 Drawing Sheet(s) Filed in Color)

COMPOSITE MAGNETIC NANOPARTICLE DRUG DELIVERY SYSTEM

RELATED APPLICATIONS

This application relates to and claims priority to U.S. Provisional Patent Application No. 61/392,018, which was filed Oct. 11, 2010, the teachings and contents of which are incorporated herein by reference in its entirety.

BACKGROUND

The present disclosure is broadly concerned with drug delivery systems. More particularly, it is concerned with drug carrying nanocomposite particles including magnetic nanoparticles and a biocompatible polymer that is biodegradable.

Conventional chemotherapies for cancers and inflammatory diseases act systemically, causing severe side effects throughout a patient's body. The cytotoxic effects are diffuse, and extend to healthy cells as well as malignant or inflamed cells. These chemotherapies also lack the ability to boost uptake of their therapeutic agents into the affected tissues, where it can be most effective. Known chemotherapies are also unable to provide slow-release delivery of pharmaceutical agents to targeted sites such as tumors and areas of inflammation.

Primary bone cancers, including osteosarcoma, chondrosarcoma, and Ewing's sarcoma, are highly malignant tumors derived from osteogenic cells or chondrocytes. Osteosarcoma is one of the most common primary malignant tumors seen in orthopedic surgery, with high mobility in young adults and adolescents. Despite intensive treatment, including adjuvant chemotherapy to localize the tumor before surgery and prevent recurrence and metastasis after surgery, wide excision of tumors, and amputation of diseased limbs, approximately half of the patients die within five years. Other cancers, such as breast, skin, liver, lung, prostate, throat and kidney, could also benefit from close targeting of chemotherapy. Recent studies have suggested that the efficiency of chemotherapy in treatment not only depends on the anti-cancer drug itself but that it is also critically associated with the drug delivery and distribution, local site concentration, and duration of effective dose. However, maintenance of effective concentrations of chemotherapy agents at a local tumor site without broadly killing remote normal cells remains an unsolved task.

Certain inflammatory diseases, such as rheumatoid arthritis (RA), experience limited treatment success with conventional chemotherapy, even when it is employed in combination with surgery and implants. RA is a chronic autoimmune disease that affects about 1% of the world population, including 1.3 million Americans. In any age group, women are affected three times more often than men. Although there are many available courses of treatment for managing the symptoms, and patients can go into remission between flares, no cure is currently available. The disease is characterized by inflammation of the lining, or synovium. After the appearance of the disease, erosive joint destruction usually starts within 1-2 years and continues. RA usually leads to long-term joint damage, resulting in chronic pain, loss of function and mobility, and disability. Although RA is most commonly known to affect joints, it is a systemic disease that can also affect organs and tissues and results in early mortality. Current therapies for RA include a range of pharmaceutical agents. Failure to respond adequately to medications and other possible treatments frequently requires surgery to correct severely affected joints. Despite intensive treatment with such drugs, most RA patients suffer for extended periods of time and experience substantial loss of function and mobility. Recent studies have suggested that the efficiency of RA drugs in treatment is critically associated with the drug delivery and distribution, local site concentration, and effective duration, none of which are effectively addressed with conventional RA chemotherapy.

Nanomaterials exhibit many novel physical properties such as optical, electronic, magnetic and structural properties, which are not found in bulk materials. These properties could enable nanomaterials to be used for detection of desired cells by covalently linked peptides, proteins, nucleic acids, and small-molecule ligands. Various attempts have been made to develop nanoparticles for use in targeted drug delivery systems. Detection is a crucial step in developing such systems since it is necessary to verify concentration of the nanoparticles at the selected location. Detection of nanoparticles used in drug delivery is problematic, however, because of the extremely small particle size. Biodegradable nanoparticles are especially difficult to detect, because of the inherent property of degradation. Once the nanoparticles are degraded, there is no residual "footprint" that can be detected, aside from the presumptive results of the drug release.

Superparamagnetic iron oxide nanoparticles have been used as contrast agents in cancer detection and have been widely studied for use in drug delivery. Metal and semiconductor nanoparticles have been used for molecular profiling studies and multiplexed biological assays. Quantum Dots (QD) have been used extensively in fluorescent probes for in vivo biomolecular and cellular imaging. However, difficulties have been reported in detecting the QD probes in living animals and QD have been reported to be toxic if allowed to aggregate on the cell surface. Attempts have been made to use amphiphilic triblock copolymer to prevent aggregation and degradation of QD within the in vivo environment. There have also been recent attempts to develop targeted therapeutic systems using external forces, including magnetic fields, ultrasound, electric fields, temperature, light, and mechanical forces to concentrate drugs in a target location. Magnetically targeted oral drug delivery of polymeric microparticles infused with magnetic nanocrystals has been shown to increase the efficiency of protein drugs used to increase bioavailability of insulin. Some problems or difficulties encountered when using currently available magnetic drug delivery systems is that the systems require amounts of magnetic material that may cause inflammation, cytotoxicity or other harm to the tissues. Such magnetic systems may also be subject to inefficiency in migration.

Albumin, the major plasma protein in human blood, plays a key role in the transport of nutrients and metabolites as well as maintenance of the colloidal osmotic pressure of blood. Previous investigations have shown that tumors and some inflammatory disorders metabolize substantial amounts of albumin. In particular, tumors and RA are known to metabolize albumin for a source of nitrogen and energy. Other studies have shown that tumor-bearing animals accumulate albumin in tumors because of their altered physiology and metabolism, including fluid phase endocytosis. Tests of the distribution of albumin in arthritis mice by injection of fluorescence-labeled human serum albumin have revealed increased labeled-albumin concentration in arthritic digits in comparison with digits without arthritis. In a scintigraphic image of the entire mouse, there was a higher concentration of labeled albumin in the kidneys and paws. Inclusion of albumin in nanocomposite materials as a targeted drug delivery system may increase the concentration of the therapeutic agent directly in the affected tissue. However, in order to develop such a system, it will be necessary to overcome the problem of organ concentration so that albumin is able to pass through organs such as kidneys and liver without absorption.

What is needed is a targeted drug delivery system and/or composition for cancers and inflammatory diseases that can deliver effective quantities of pharmaceutical agents to closely targeted sites and release them in a controlled manner over an extended period of time. What is also needed is a system or composition comprising a polymer, preferably a biodegradable polymer, a biological targeting composition, a magnetic nanoparticle, and a drug. What is further needed is such a system or composition involving a biodegradable polymer, a biological targeting component, a magnetic nanoparticle, and a cancer drug for the treatment of cancers with aggressive tumors such as bone cancer. What is still further needed is such a system or composition involving a biodegradable polymer, a biological targeting component, a magnetic nanoparticle and an RA drug for the treatment of inflammation in RA. What is also needed is an anti-cancer or RA drug-carrying magnetic nanocomposite that will migrate to a local tumor site or site of inflammation by both external force such as a high magnetic field, an internal force, such as interaction of a biological targeting component with the tumor or affected tissues, or both, and subsequently release the drug in a targeted and concentrated manner. What is still further needed is a biological targeting agent that will reduce the amount of magnetic nanoparticles used during the fabrication of the composite nanoparticle thereby reducing interaction between the magnetic agent and the tumor or site of inflammation. There is also a need for a biological targeting agent that can be used in a composite nanoparticle drug delivery system to draw a drug directly into the affected tissue. What is still further needed is a highly concentrated and persistent antitumor or inflammatory agent that will slow or halt the growth of aggressive primary tumors such as osteosarcomas and prevent tumor metastasis and inflammation.

SUMMARY OF INVENTION

The present invention overcomes the problems and deficiencies in the prior art and provides nanoparticles for medical use that have a dual targeting system for precise placement and tissue uptake, and that can provide controlled delivery of a therapeutic pharmaceutical agent over an extended period of time.

Generally, the composite nanoparticles include a biocompatible and biodegradable synthetic resin material and a biological targeting agent. Preferably, the composite nanoparticles further include magnetic nanoparticles and/or a therapeutic pharmaceutical agent. Still more preferably, the composite nanoparticles include a biocompatible and biodegradable synthetic resin material, a biological targeting agent, magnetic nanoparticles, and a therapeutic pharmaceutical agent. Poly(lactic-co-glycolic acid) or poly(D,L-lactide-co-glycolide) or PLGA is a particularly preferred synthetic resin material because it is biocompatible and approved for use in vivo by the U.S. Food and Drug Administration, and it is biodegradable as well. Because PLGA degrades in the body by hydrolysis of the ester linkages to the original monomers, the time required for degradation may be controlled by altering the ratio of monomers used during PLGA synthesis. PLGAs are identified in accordance to the ratio of monomers used, e.g. PLGA 75:25 identifies a copolymer having 75% lactic acid and 25% glycolic acid. Each of the monomers of PLGA can be present in an amount from about 15% to about 85%, more preferably from about 20% to about 80%, still more preferably from about 25% to about 75%, even more preferably from about 30% to about 70%, still more preferably from about 35% to about 65%, even more preferably from about 40% to about 60%, still more preferably from about 45% to about 55%, and most preferably about 50%. Other preferred synthetic resin materials which may be employed include chitosan, poly(lactic acid) or PLA, poly(glycolic acid) or PGA, polycaprolactone (PCL) or any other suitable synthetic resin material that is both biocompatible and biodegradable.

Any magnetic or magnetized nanoparticle can be used for purposes of the present invention The preferred magnetic nanoparticles are magnetite ($Fe_3O_4$), although cobalt ferrite or other suitable magnetic material or combinations of magnetic materials may be employed.

Advantageously, use of a biological targeting agent in the magnetic nanoparticle drug delivery system serves to increase the targeting efficiency for the pharmaceutical agent while reducing the requisite quantity of magnetic nanoparticles, which may be toxic at elevated concentrations. Human serum albumin is a particularly preferred biological targeting agent component.

A wide variety of therapeutic pharmaceutical agents may be employed, either alone or in combination, including but not limited to anticancer drugs and autoimmune/anti-inflammation drugs, disease modifying anti-rheumatic drugs (DMARDs), anti-inflammatory medications, anti-malarial medications, biological response modifiers, corticosteroids and cyclooxygenase-2 (COX-2) inhibitors. Specific pharmaceutical agents include, but are not limited to methotrexate (MTX), 5-Fluorouracil (5-FU), doxorubicin, epirubicin (FEC), cyclophosphamide, docetaxel, doxorobicin, paclitaxel and cisplatin. Some drugs, particularly MTX, exhibit dual therapeutic activity for both cancer and arthritis. Those skilled in the art will appreciate that virtually any pharmaceutical composition, including those not yet known or not yet known to exhibit a particular therapeutic activity, may be employed in the present nanoparticle drug delivery system. A combination of one or more pharmaceutical compositions may be employed.

The composite nanoparticles have a diameter of from about 40 nm to about 1.5 µm, more preferably from about 50 nm to about 1.2 µm, even more preferably from about 60 nm to about 1 µm, still more preferably from about 70 nm to about 800 nm, even more preferably from about 80 nm to about 600 nm, still more preferably from about 90 nm to about 400 nm, even more preferably from about 100 nm to about 200 nm. Further, it is understood that the size of the composite nanoparticle is inversely related to the release rate of the pharmaceutical agents. In other words, as the size of the composite nanoparticle increases, the release rate is slowed or prolonged and as the size of the composite nanoparticle decreases, the release rate is increased. This is a function of the surface area:volume ratio of the composite nanoparticle. The preferred composite nanoparticles include from about 5% to about 95% of the synthetic resin material, preferably PLGA (w/v), more preferably from about 10% to about 85% PLGA (w/v), still more preferably from about 15% to about 75%, even more preferably from about 20% to about 70%, still more preferably from about 25% to about 65%, even more preferably from about 30% to about 50%, and most preferably being between 35% to about 40% PLGA. The preferred PLGA has a molecular weight of from about 40,000 to about 75,000. When magnetic nanoparticles are included in the composition, they can be present in an amount from about 0.5% to about 50%, more preferably from about 1% to about 40%, even more preferably from about 2% to about 30%, still more preferably from about 3% to about 20%, even more preferably from about 4% to about 10%, and most preferably about 5% as such a percentage has been shown to generally provide sufficient magnetic attraction while avoiding toxicity issues. These magnetic nanoparticles are generally from about 4 nm to about 25 nm in diameter, more preferably from about 5 nm to about 20 nm, with a particularly preferred diameter of about 10 nm.

The amount of albumin in the composite nanoparticles can range from about 5% to about 85% albumin (v/v), more preferably from about 10% to about 80%, still more preferably from about 15% to about 80%, even more preferably from about 20% to about 70% albumin (v/v), still more preferably from about 25% to about 60%, even more preferably from about 30% to about 50%, and most preferably from about 35% to about 40%. The amount of pharmaceutical agent will depend on the type of drug selected for inclusion in the composite nanoparticles. However, it is known that the pharmaceutical agent can comprise up to 80% of the nanoparticle, but generally, the amount included will be much less.

Depending on their intended use, composite nanoparticles may also be prepared to include only selected ones of the previously described components. In one embodiment they may include a biocompatible, biodegradable synthetic resin material such as PLGA, a biological targeting agent such as albumin and a pharmaceutical composition. In another embodiment, they may include a biocompatible, biodegradable synthetic resin material such as PLGA, a magnetic nanoparticle such as magnetite nanoparticles and a pharmaceutical composition. In yet another embodiment, they may include a biocompatible, biodegradable synthetic resin material such as PLGA, a magnetic nanoparticle such as magnetite and a biological targeting agent such as albumin. In still another embodiment, the composite nanoparticles may include a biocompatible, biodegradable synthetic resin material such as PLGA and a biological targeting agent such as albumin.

The composite magnetic nanoparticles may be produced by an emulsion/solvent evaporation technique. The magnetic nanoparticles are preferably produced by a coprecipitation technique. Hydrochloric acid and ammonium hydroxide solutions are prepared followed by addition of ferric chloride and ferrous chloride salts dissolved in hydrochloric acid. The two solutions are combined while stirring vigorously, preferably at about 1,200 rpm. While continuing to stir, ammonium hydroxide solution is added drop-wise. Preferably the addition occurs within 5 minutes at room temperature. Magnetite nanoparticles form, which particles have a diameter of from about 5 nm to about 15 nm. In other preferred aspects, a sol-gel process may be employed instead of a coprecipitation method to fabricate other magnetic nanoparticles, such as, for example, $CoFe_2O_4$ nanoparticles. In another preferred method of preparing composite magnetic nanoparticles in accordance with the present invention, the composite magnetic nanoparticles are generally prepared by providing a quantity of a solvent, dissolving a quantity of a synthetic resin polymer composition in the solvent to form a polymer matrix, dissolving a quantity of a biological targeting agent in a quantity of solvent to form a biological targeting agent solution, adding the polymer matrix to the biological targeting agent solution to form a mixture, providing a quantity of magnetic nanoparticles, adding the magnetic nanoparticles to the mixture to form a first oil phase, providing a quantity of a surfactant, adding a quantity of oil, preferably paraffin oil, to the surfactant to form a second oil phase, mixing the second oil phase at high shear, adding a quantity of the first oil phase to the second oil phase, preferably in a dropwise fashion, mixing to form magnetic nanocomposite particles, washing the composite magnetic nanoparticles in a solvent, and drying the composite magnetic nanoparticles. Another preferred method of preparation of composite magnetic nanoparticles comprises the steps of providing a quantity of an acetonitrile solvent, dissolving a quantity of poly(lacto-co-glycolic acid) in the acetonitrile solvent to form a polymer matrix, dissolving a quantity of human serum albumin in a quantity of acetonitrile solvent to form an albumin solution, adding the polymer matrix to the albumin solution to form a mixture, providing a quantity of magnetite nanoparticles, adding the magnetite nanoparticles to the mixture to form a first oil phase, providing a quantity of a surfactant, adding a quantity of paraffin oil to the surfactant to form a second oil phase, mixing the second phase at high shear, adding dropwise a quantity of the first oil phase to the second oil phase, mixing to form magnetic nanocomposite particles, washing the composite magnetic nanoparticles in a solvent, and drying the composite magnetic nanoparticles. In preferred forms, the methods of preparing the composite nanoparticles further includes the step of adding a quantity of a pharmaceutical composition with the magnetite nanoparticles to the mixture. In other preferred forms, the method will further include the step of providing a dispersing agent for changing the surface energy and/or surface charge of the nanoparticles to aid in dispersion of the nanoparticles in the polymer matrix. Preferably, the dispersing agent is selected from the group consisting of surfactants, polymers and electrolytes. Still more preferably, the dispersing agent is selected from the group consisting of citric acid, tetramethyl ammonium hydroxide, gum Arabic, sodium dodecyl sulfate, and mixtures thereof.

In yet another preferred method of making or preparing nanoparticles in accordance with the present invention, a nanoparticle is prepared by combining a synthetic resin polymer composition with a biological targeting agent; mixing said synthetic resin polymer composition with said biological targeting agent; and forming nanoparticles under high shear conditions. Preferably, the method also includes the step of adding a quantity of magnetic nanoparticles to the synthetic resin polymer composition and the biological targeting agent. In preferred forms the synthetic resin polymer composition is PLGA and the biological targeting agent is albumin. When albumin is used, it is preferred to use human serum albumin. Preferred magnetic nanoparticles are magnetite. In other preferred forms, the general method also includes the step of adding a quantity of a pharmaceutical composition to the synthetic resin polymer composition and the biological targeting agent Nanoparticles tend to aggregate due to intermolecular interactions, such as electrostatic, hydrophobic, and van der Waals forces, which enhances the difficulty of dispersion in biodegradable polymer matrices. Effective utilization of nanoparticles in drug-carrying nanocomposite particle fabrications strongly depends on their ability to disperse homogeneously throughout the matrix and to achieve good interfacial bonding, which will affect the overall performance of these novel materials. For these reasons, surface energy and surface charge of the nanoparticles are changed by additions of various chemicals or dispersing agents such as surfactants, polymers and electrolytes. Preferred dispersing agents include, but are not limited to, citric acid, tetramethyl ammonium hydroxide (TMAH), gum Arabic, and/or sodium dodecyl sulfate (SDS) and mixtures thereof. Any suitable chemical capable of changing the surface energy and surface charge of the nanoparticles may also be employed. Ultrasonic vibration, high shear mixing, and mechanical stirring are preferably used to disperse the modified nanoparticles into the matrix materials.

A first oil phase (phase 1) is formed consisting of a pharmaceutical compound, a biocompatible, biodegradable synthetic resin material, magnetic nanoparticles and a biological targeting agent dispersed in a solvent by sonication. In a preferred aspect, ultrasonic vibration, mechanical stirring and high shear mixing are used to disperse the modified nanoparticles into the polymer matrix. In another preferred aspect, the previously described chemicals are added to change the surface energy and surface charge of the nanoparticles to facilitate their dispersion homogeneously throughout the biodegradable polymer matrix. A second oil phase (phase 2) is formed consisting of paraffin oil and a surfactant. Phase 2 is placed in a container and positioned under a fast rotating blade. The preferred rotating blade is a high shear impeller operated at about 7000 rpm. Phase 1 is added dropwise to phase 2 and the rotating blade shears the droplets into small composite structures, which may be generally spherical shape. The surfactant aids in this process and the oil prevents the newly formed structures from agglomerating. The nanocomposite particles are preferably collected by centrifuging and solvent washed until they are residue free. In a preferred aspect, the composite nanoparticles are washed four times with a solvent such as n-hexane and/or carbon tetrachloride.

In a method of use, magnetic composite nanoparticles are provided which include a biocompatible and biodegradable polymer, magnetic nanoparticles, a biological targeting component, and an FDA approved therapeutic pharmaceutical composition. A solution of the composite nanoparticles in sterile saline is prepared and a quantity of the solution is injected into an affected area of a patient such as a cancerous tumor or inflammation. In a preferred aspect the solution contains $10^5$ nanoparticles loaded with a pharmaceutical composition. In another preferred aspect of use, the solution of composite nanoparticles is administered to a patient via inhalation, oral, parenteral, transmucosal, nasal, colorectal, pulmonary, cardiovascular or intraosseous infusion or combination thereof. In still another preferred aspect of use, the solution of composite nanoparticles is administered via a catheter.

In a preferred aspect of the method of use, one or more magnets is positioned in or adjacent to an affected area such as a cancerous tumor or inflammation site. In another preferred aspect, the magnet is surgically implanted into the body of a patient. The composite nanoparticle solution is injected into the affected area or otherwise delivered as previously described. Advantageously, the composite nanoparticle drug delivery system provides a dual targeting mechanism for drug delivery. The magnetic composite nanoparticles are attracted by the magnet(s) to the affected area, and the biological targeting component draws the nanoparticles into the tissues within of the affected area. As the biodegradable polymer breaks down, it releases the drug in a controlled, timed-release manner into the tissues of the targeted area.

The present invention also provides a method of localized cancer therapy. The method generally includes the steps of providing a composite magnetic nanoparticle including poly(lacto-co-glycolic acid), magnetite, human serum albumin and a pharmaceutical composition, positioning magnets adjacent a cancerous tumor of a patient, injecting a quantity of the composite magnetic nanoparticles into the bloodstream of the patient, and positioning a magnet adjacent the cancerous tumor.

The present invention further provides a method of treating an inflammatory condition or cancer generally comprising the steps of administering a nanoparticle composition comprising a synthetic resin polymer, a pharmaceutical composition, and a biological targeting agent. In preferred forms, the method further comprises the step of combining a magnetic nanoparticle with said nanoparticle composition prior to the administration thereof. Preferably, the synthetic resin polymer composition is PLGA and/or the biological targeting agent is albumin. When albumin is the biological targeting agent, it is preferred to use human serum albumin. Additionally, it is preferred to use magnetite as the magnetic nanoparticles.

The composite magnetic nanoparticle drug delivery system may be used in this manner to treat inflammatory diseases such as RA and other forms of arthritis, cancers, such as, for example, bone cancer, breast cancer, skin cancer, prostate cancer, liver cancer, lung cancer, throat cancer and kidney cancer. The system may also be used to protect against bacterial infections of implants, to treat nerve damage, lung, liver and kidney diseases, eye treatment, spinal cord injuries, heart disease, arterial disease.

Those skilled in the art will appreciate that therapeutic use of the disclosed targeted drug delivery system should not be limited to the foregoing and that it may be used to treat or prevent any cancer, disease or condition.

DESCRIPTION OF THE FIGURES

The patent or application file contains at least one drawing executed in color. Copies of this patent or patent application publication with color drawings will be provided by the Office upon request and payment of the necessary fee.

FIG. 1A top Panel is a fluorescent image of a drug at low concentration;

FIG. 1A bottom Panel is a fluorescent image of a drug at low medium concentration;

FIG. 1B top Panel is a fluorescent image of a drug at high medium concentration;

FIG. 1B bottom Panel is a fluorescent image of a drug at high concentration;

DETAILED DESCRIPTION

Figure 1A:
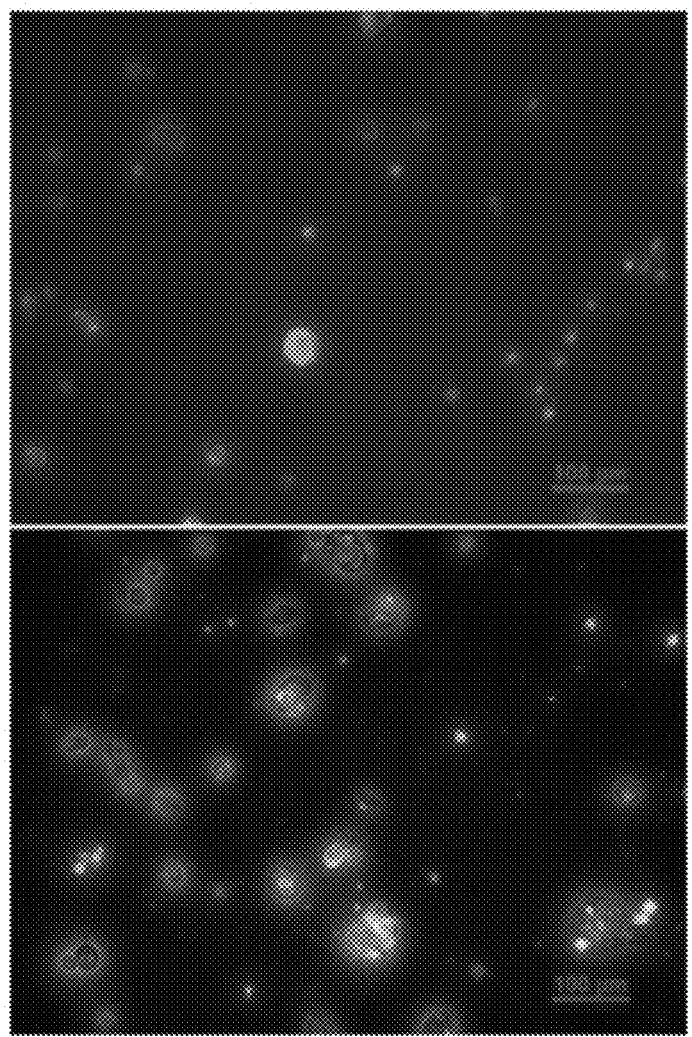
Figure 1B:
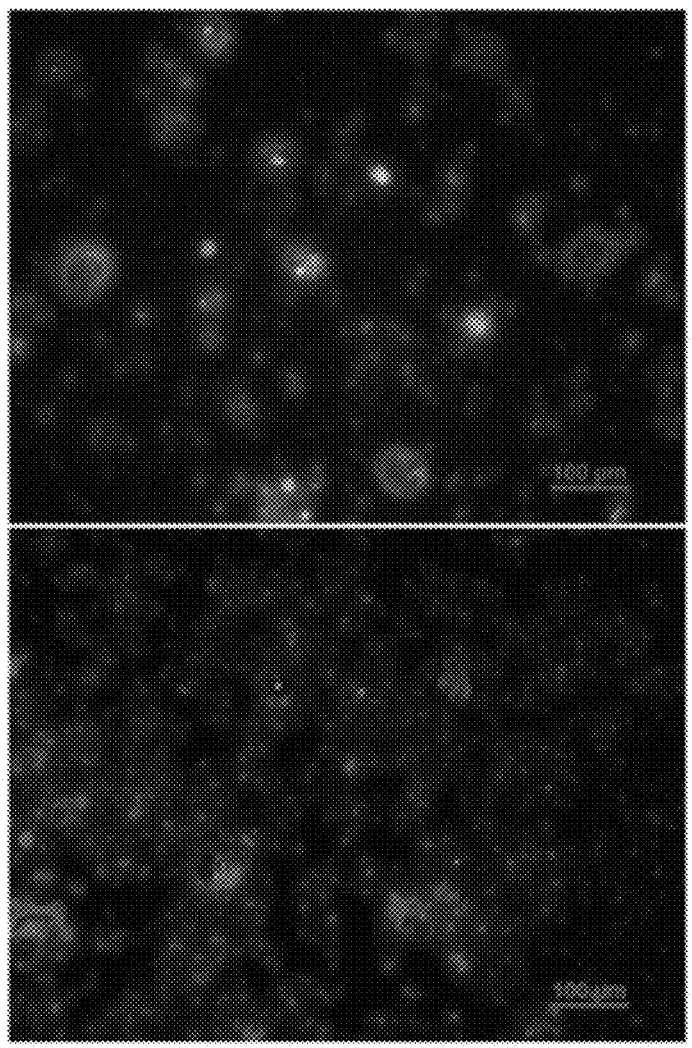

The following examples are representative of preferred embodiments of the present invention. It is understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the invention in virtually any appropriately detailed embodiment.

Example I

In Vivo Studies of Drug Carrying Magnetic Nanocomposite Particles Via Fluorescent Molecules Because novel nanomaterials may have toxic effects, the ideal detection method would employ a well-established and known biocompatible material. 1,6-Diphenyl-1,3,5-hexatriene (DPH) is a commonly used fluorescent dye used in assessment of cell membranes. The molecule is hydrophobic in nature, and has emission maximum at 428 nm and lower maxima at 452 and 405 nm in phosphate buffer/ Sodium Dodecyl Sulfate pH 7.0. It is shown in this example that encapsulations of the fluorescent molecule in the polymeric nanoparticles leaves a footprint that may be used to identify where the biodegradable delivery system has been.

Materials and Methods

An oil-in-oil emulsion/solvent evaporation technique was used to fabricate magnetic nanocomposite spheres. This evaporation technique consists of two phases including aqueous phase and oil phase. Delivery efficiency and therapeutic effects of an albumin-rich nanocomposite sphere drug delivery system to squamous-cell carcinoma (SCC) were evaluated using a nude mouse model. Nanocomposite spheres were made by an oil-in-oil (O/O) emulation technique.

Magnetic Nanoparticle Synthesis

Magnetite ($Fe_3O_4$) nanoparticles were prepared using 50 ml of 2 M HCl (36.5%-38%) and 55 ml of 5 M ammonium hydroxide (NKOH) (28-30%) solutions in a 100 ml beaker. In separate beakers, 2.00 g of ferric chloride ($FeCl_3.6H_2O$) was dissolved in 40 ml of 2 M HCl, and 1.25 g of ferrous chloride ($FeCl_2.4H_2O$) was dissolved in 10 ml of 2 M HCl. The two solutions were then combined and stirred vigorously at 1,200 rpm. Next, 55 ml of 5 M ammonium hydroxide was added drop-wise in five minutes at room temperature. The magnetite nanoparticles were collected using a strong Nd—Fe—B magnet, washed several times with DI water, and dried at room temperature. The magnetite nanoparticles exhibited an average diameter of about 10 nm.

Composite Magnetic Nanoparticle Synthesis

In the nanocomposite sphere fabrication process, two dissimilar oil phases are prepared. During the first oil phase, 1.25% w/v of PLGA 50:50 (mw 40,000-75,000) was added to 5 ml of acetonitrile solvent placed in a conical flask with a stopper. The mixture was kept on a hotplate for 20-30 minutes to dissolve the PLGA completely in the acetonitrile, using a small magnetic bar. At different weight ratios, commercially available human serum albumin, the pharmaceutical composition 5-FU and the fluorescent marker DPH were also dissolved in acetonitrile and added to the previous solution. The magnetic bar was removed before known amounts of magnetic nanoparticles were added to the PLGA/albumin/DPH solution. Afterwards, the flask was placed in a sonicator for about 10-15 minutes (or until the MNPs were completely dispersed).

Figure 18:
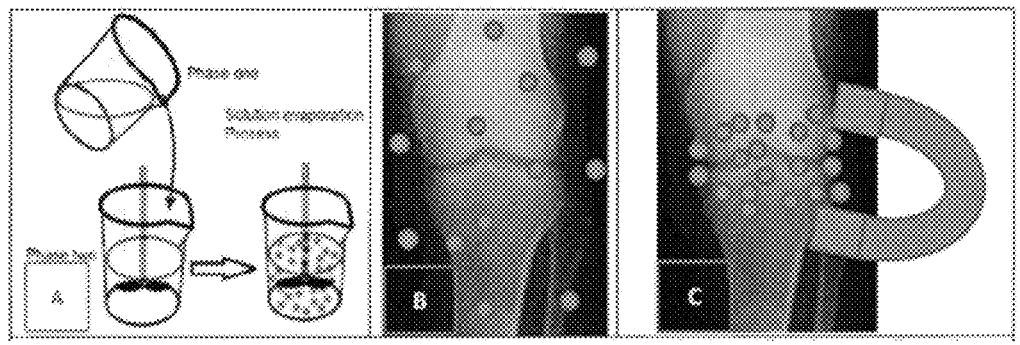
FIG. 18 is a schematic representation of a single oil-in-oil emulsion/solvent evaporation method (left Panel); a schematic illustration of nanocomposite spheres without a magnetic field (center Panel); and a schematic representation of magnetic targeted drug delivery for a RA treatment (right Panel)
Figure 19:
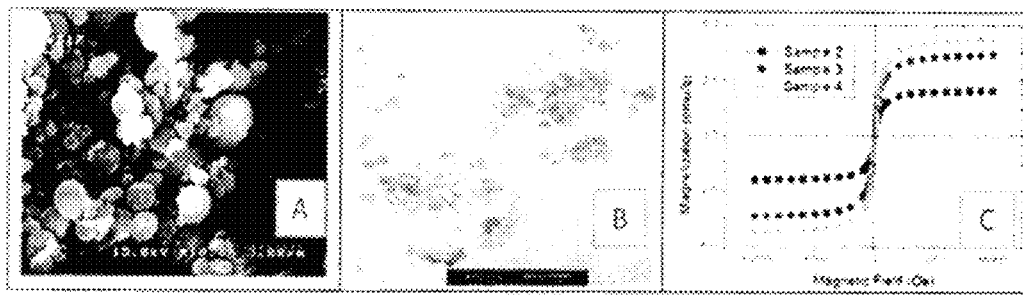
FIG. 19 is a SEM image showing size and shapes of Sample 2 (left Panel); a TEM image of drug-carrying nanocomposite spheres in PLGA matrix (center block) and SQUID data of magnetic nanocomposite spheres obtained at 5,000 Gauss and 300K (right Panel)
Figure 20:
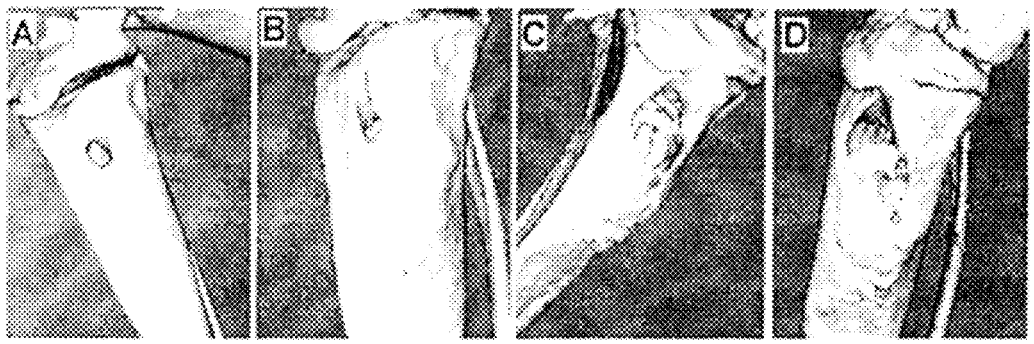
FIG. 20 shows MicroCT 3-dimensional images of tibia harboring experimental tumors after tumor cell inoculation: after 7 days (panel A), after 3 weeks (Panel B), after 5 weeks (Panel C), after 8 weeks (Panel D)
Figure 21:
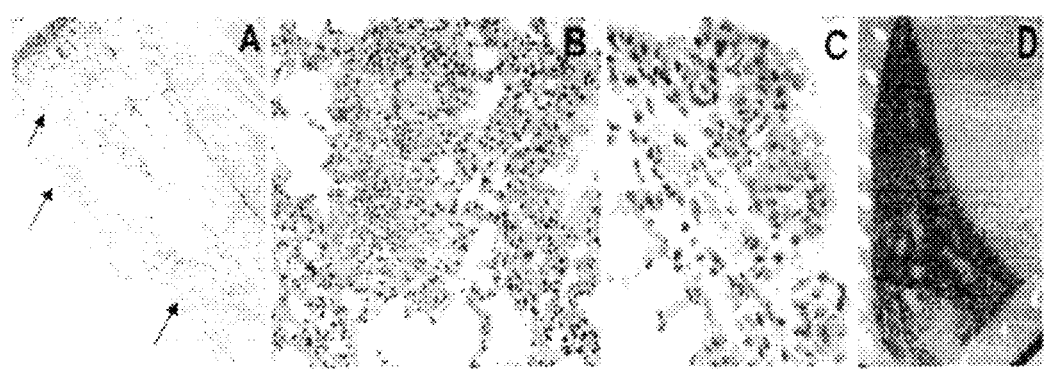
FIG. 21 is histological images of orthotropic tumor development in the proximal tibia at 6 weeks (Panel A); dispersive lung metastasis lesions at 6-8 weeks (Panels B and C); typical lung metastatic nodules on lung CT images at 56 days after orthotropic osteosarcoma cell injection (Panel D)

The second oil phase was prepared by adding 1% v/v of Span 80 as a surfactant to 40 ml of heavy liquid (paraffin oil). This mixture was then placed under an overhead mixer operated at 7,000 rpm with a specially designed high-shear, sharp impeller. Approximately 3 ml of the first phase was then added drop-wise to the second phase using a burette. The mixer was allowed to run for 1 hour and 30 minutes to evaporate acetonitrile and form magnetic nanocomposite particles in the viscous, heavy oil at the high shear speed. Nanocomposite particles (<2 μm) were collected by centrifugation at 17,000 rpm for 30 minutes at 10° C. and washed four times with n-hexane to completely remove the heavy paraffin oil. FIG. 18A shows a schematic illustration of magnetic nanocomposite sphere fabrication. The resulting particles were filtered using a 200 nm filter medium under a 25 in Hg vacuum, and dried prior to the characterization tests.

The nanocomposite sphere drug delivery system thus prepared has five components: 39% PLGA, 39% Albumin, 20% 5-FU, 1% Nano-Magnetite particles and 1% 1,6-Diphenyl-1,3,5-hexatriene (DPH). In this experiment, PLGA was used to control the release rate of the therapeutic agent (5-FU), while fluorescent marker (DPH) was incorporated to trace the nanocomposite trafficking. Albumin and Nano-Magnetite particles were included into the nanocomposite spheres as the driving forces to targeted deliver anticancer drug to the tumor site. This study did not introduce an external magnetic force into the system, but rather assessed the fluorescence footprint left behind by the release of DPH from the drug carrier system.

In Vitro

To identify the feasibility of a fluorescent encapsulated nanoparticle drug carrier system, SCC cells were cultured with varying concentrations of the fluorescent carrier system. A fluorescent microscope was used to visualize the fluorescence response of the cell/drug carrier system. Green and Red fluorescent images were taken and overlaid for analysis. Where the green and red fluorescent wavelengths were seen, the mixture of the two colors produced yellow. By varying the concentration of the drug carrier system, the green fluorescent is visible at lower drug carrier concentrations than the higher concentrations. At higher concentrations, after two days the fluorescent images are dominated by the red spectrum. On closer inspection, the drug carrier system shows higher intensity in the red spectrum and cells show a higher intensity in the green spectrum, as shown in the fluorescent images of FIG. 1A, top and bottom Panels.

In Vivo

Figure 2:
FIG. 2 is a histology image of a control tumor.
Figure 3:
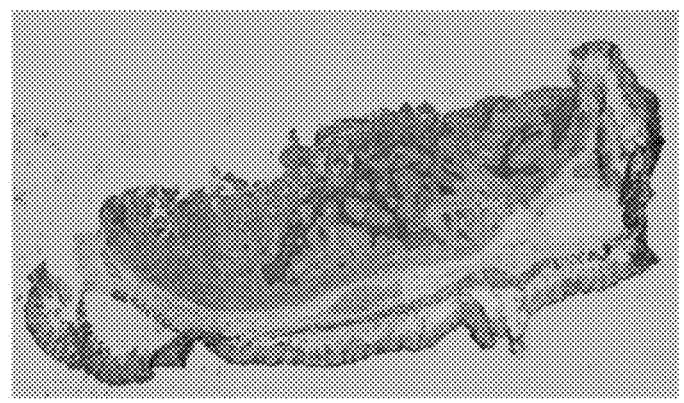
FIG. 3 is a histology image of a tumor following treatment.

In this experiment, human SCC tumors were established by subcutaneous inoculation of SCC cells, respectively, on left and right dorsal sides of nude mice (n=5). Two weeks after SCC tumor development, 0.5 ml of the chemotherapy nanocomposite particles (3 mg/ml solution) were injected in 4 mice around the left side tumor at 2-day intervals for 12 days. One tumor-bearing control mouse without treatment was sacrificed 7 days earlier than the counterpart mice due to the fast-growing of the tumor. The mice were monitored daily for tumor growth and general health; and sacrificed on the $12^{th}$ day. Tumors were harvested and prepared for frozen and paraffin-embedded sections. The tissue of the tumor before treatment is shown in FIG. 2, and the tissue following treatment is shown in FIG. 3. The four mice injected with the drug carrier system did not show any significant increase or decrease in tumor size. The control mouse had an abnormally larger tumor then the treated mice.

Figure 4:
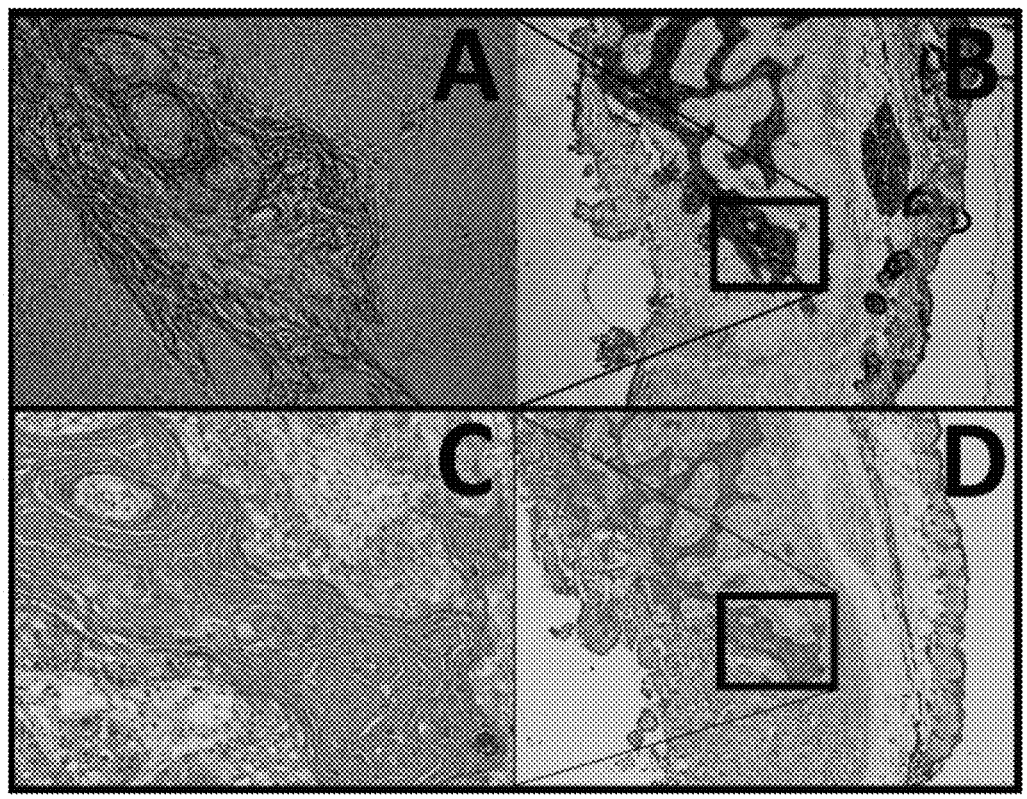
FIG. 4A is a fluorescent image at 10× magnification.
FIG. 4B is a fluorescent image at 2× magnification.
FIG. 4C is a dyed image at 10× magnification.
FIG. 4D is a dyed image at 2× magnification.

Since fluorescence (DPH) was encapsulated into the drug delivery system, it is expected that the locations of the drug release would be marked by fluorescence. Comparison of the tissue specimens under a fluorescence microscope with the H&E stained sections clearly shows penetration of the fluorescence into tumor tissue, and especially concentration in many keratin-rich areas within tumor tissue. As shown FIGS. 4 (A) and (C), the fluorescence concentrated areas correlate with the keratin-like areas. The cells in these areas exhibited cell membrane disruption and nuclear disappearance, and cell debris was ubiquitous. 5-FU is a well established chemo-agent for SCC. The fluorescent "footprint" shown in FIG. 4 and the presence of dying cells suggest infiltration of the carrier system into the center of the tumor.

Figure 5:
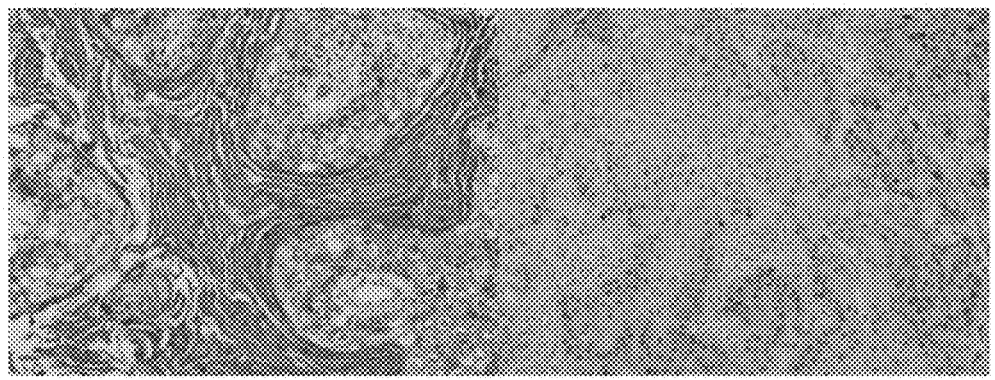
FIG. 5 is a 10× microscopic image of the treated tumor showing signs of cell death (left panel), and a 10× microscope image of the control tumor showing signs of health cancer cells (right panel)

Comparison of the control tumor and the treated tumor demonstrates two main differences. First, there are more keratin-like areas in the treated tumor. Second, the cells in the keratin show signs of cell death (FIG. 5 left Panel), while the control shows signs of healthy cells (FIG. 5, right Panel).

Figure 6:
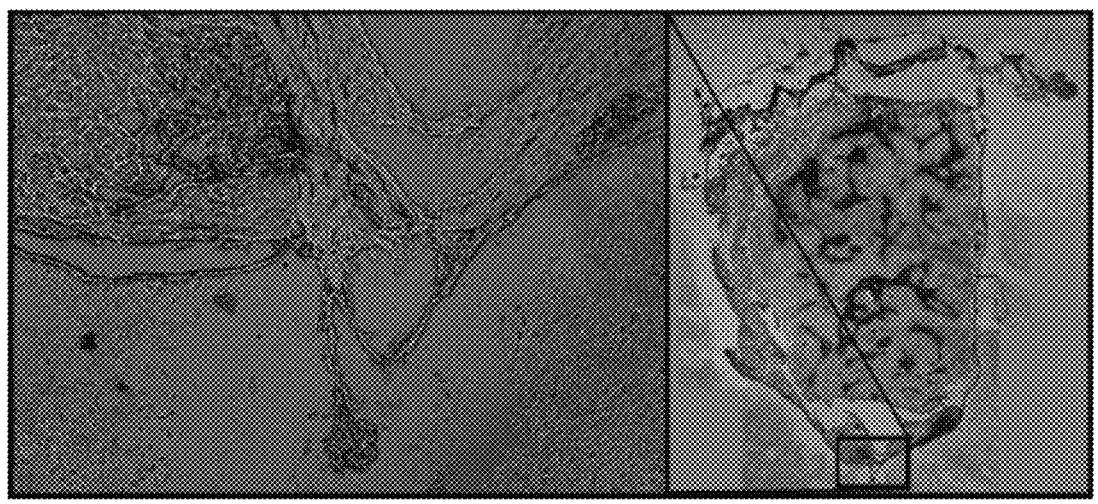
FIG. 6 is a fluorescent image at 10× objective (left panel) of the tumor shown on the right panel.

Communication between the right and left tumors on the mouse was also tested. The drug delivery system was injected next to the tumor on the left side. In order for the fluorescence and 5-FU effects to be seen on the right tumor, there must be communication by the drug carrier system from the left side of the mouse to the right side of the mouse. Evidence of fluorescence and keratin was observed on the right side tumor as shown in FIG. 6. The left and right tumor on a mouse exhibits the same morphology, signifying that the location where the drug carrier system is injected may not be critical.

Conclusion

This study demonstrates that encapsulation of the fluorescent molecule DPH into a nanoparticle drug carrier system may be used to leave a "footprint" of where the drug carrier system was. The fluorescent wavelengths or colors appeared to be different in an in vitro environment, depending on whether the fluorescent molecule was encapsulated in the drug carrier system (red) or SCC cell (green). Fluorescent signals have also been successfully utilized as a marker for identifying the location of the drug release by the delivery system. The fluorescent "footprint" of the nanoparticle drug delivery system indicates the existence of nanoparticle trafficking from the left tumor to the right tumor. By using fluorescent "footprints", the localization and distribution of the biodegradable drug carrier system can be identified in an in vivo environment. Upon release of the therapeutic payload in the nanoparticles including the fluorescent molecule, it is possible to characterize and evaluate the targeted drug delivery system.

Example II

Magnetic Targeted Drug Delivery System for Rheumatoid Arthritis

A magnetic targeted drug delivery system for rheumatoid arthritis consists of an FDA approved therapeutic agent, magnetic nanoparticles, a biocompatible and biodegradable polymer and a biological targeting component combined using an oil-in-oil emulsion/solvent evaporation technique. A two-phase polymeric drug delivery system targets the drug carrying nanocomposite particles to the joints of RA patients.

Materials and Methods

Figure 7:
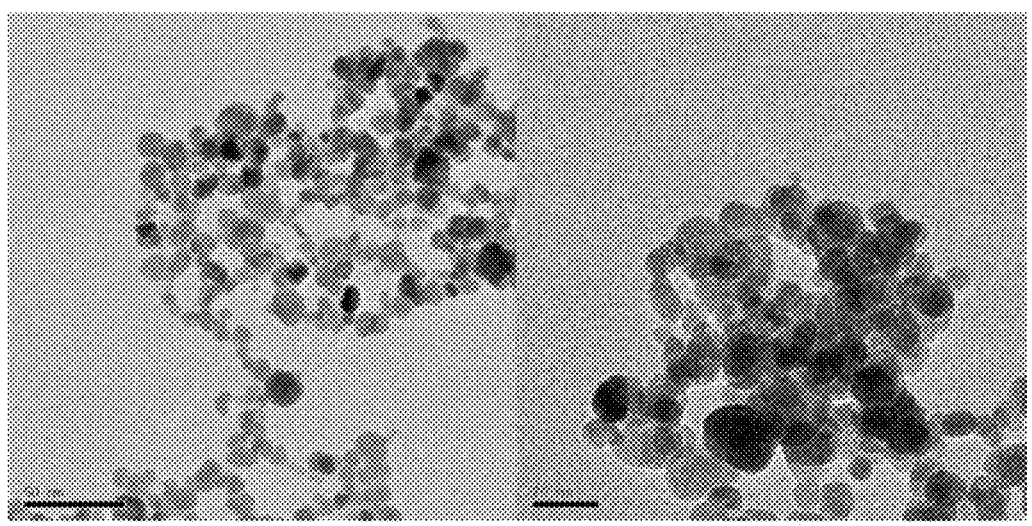
FIG. 7 is TEM images of the magnetite nanoparticles at low magnification on the left and high magnification on the right.

Composite nanoparticles were formed using the oil-in-oil emulsion/solvent evaporation procedure described in Example I in which a first phase (consisting of the key components of the spheres) was added to a second phase (consisting of paraffin oil and a surfactant) in the presence of a rotating blade. As shown in FIG. 7, the black magnetite nanoparticles which formed had a diameter of approximately 5-15 nm.

TABLE 1

Batches With Varying Weight Percentages of Albumin and PLGA

| Batches | Albumin (%) | PLGA (%) | MTX (%) | Magnetic Nanoparticles (%) |
|---|---|---|---|---|
| 1AB | 5 | 85 | 5 | 5 |
| 2AB | 15 | 75 | 5 | 5 |
| 3AB | 25 | 65 | 5 | 5 |
| 4AB | 40 | 50 | 5 | 5 |
| 5AB | 45 | 45 | 5 | 5 |
| 6AB | 65 | 25 | 5 | 5 |

Phase 1 consisted of the pharmaceutical compound (MTX), the biodegradable/biocompatible polymer (PLGA) and the two targeting compounds (magnetite and albumin). These four components were dispersed in acetone by sonication. In order to determine the optimum composition of the drug delivery system, the weight percentages of these components were varied systematically and the resulting batches were evaluated. Earlier tests had shown 5% magnetite to provide sufficient magnetic attraction, so this was held constant in each batch. The dosage of the pharmaceutical compound was likewise held constant at 5% and the optimum percentage of albumin and PLGA was studied.

Phase 2 consisted of paraffin oil and the surfactant Span 80. A tall glass containing phase 2 was placed under a blade rotating at 1700 rpm, and phase 1 was added dropwise with a syringe. As phase 1 was added, the force of the rotating blade caused each droplet to sheer into multiple, small, spherical shaped composite structures.

The nanocomposite particles were collected by centrifuging at 7,000 rpm at 10° C. for 20 minutes. The particles were then washed with a solution of hexane and petroleum ether (95:5) and centrifuged again. The washing step was repeated until all residues were completely removed form the spheres. Finally the particles were washed again with a solution of hexane and carbon tetrachloride (95:5). A 200 nm filter was used to collect the particles using vacuum filtration.

Results and Discussion
Size and Shapes

Figure 8:
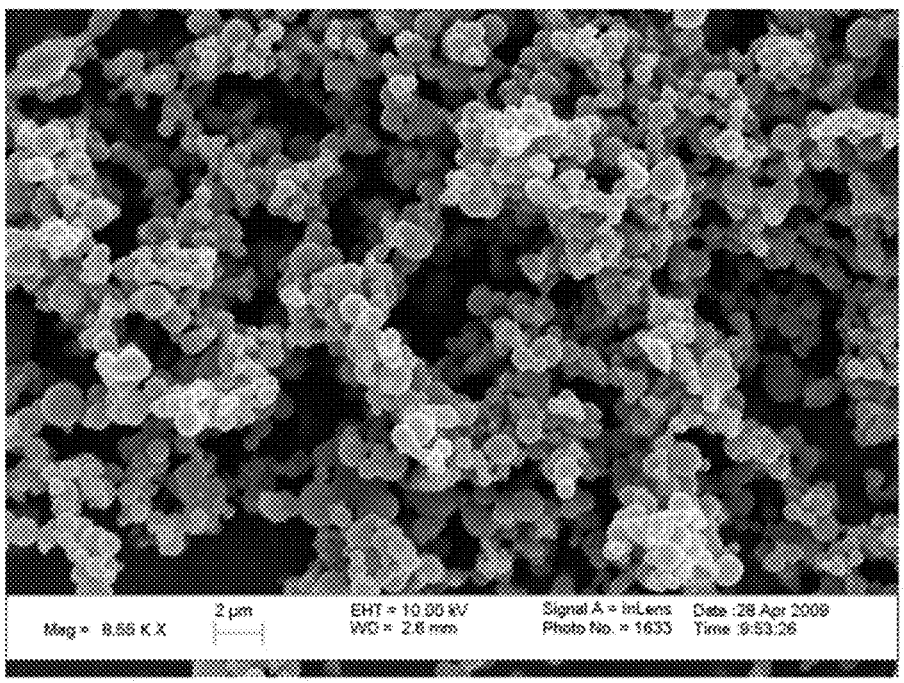
FIG. 8 is a scanning electron micrograph (SEM) image of sample 2AB containing 5% MTX, 5% magnetite, 15% albumin and 75% PLGA.
Figure 9:
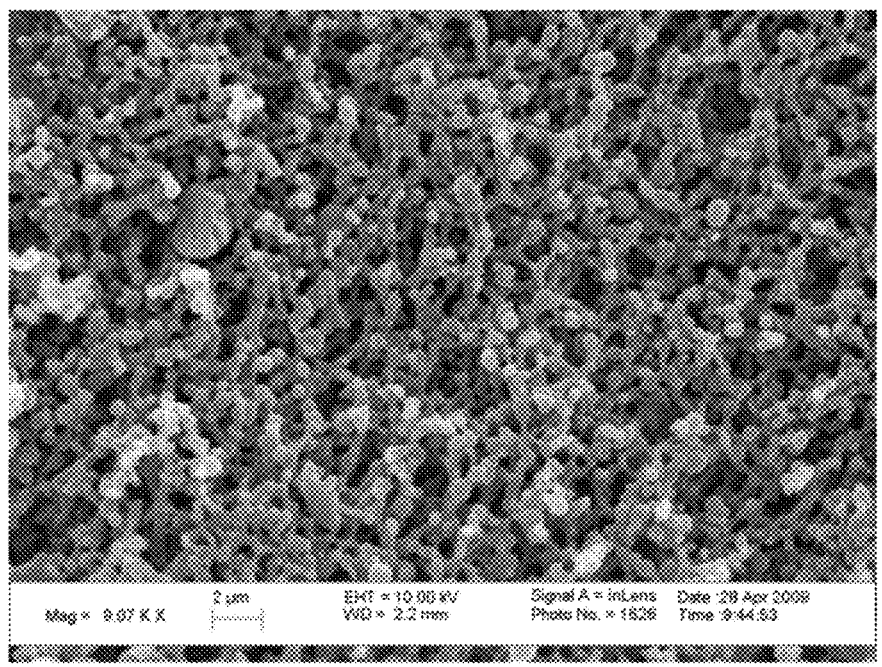
FIG. 9 is a SEM image of sample 5AB containing 5% MTX, 5% magnetite, 45% albumin and 45% PLGA.
Figure 10:
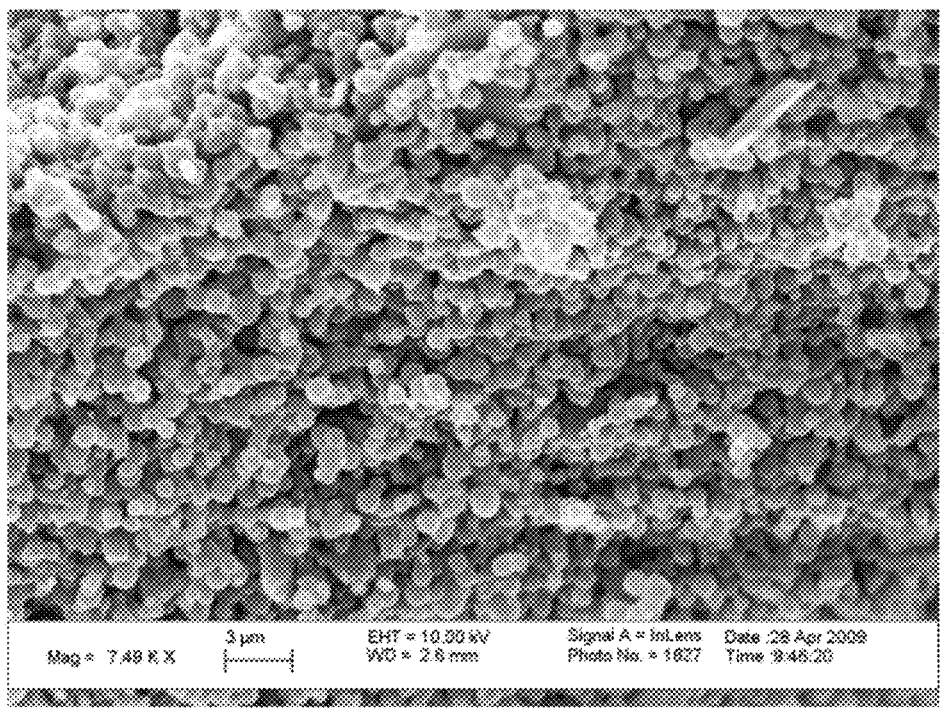
FIG. 10 is a SEM image of sample 6AB containing 5% MTX, 5% magnetite, 65% albumin and 25% PLGA.

A number of experiments were conducted to prepare various nanocomposite particles in the presence and absence of drug molecules (MTX). The size and shape, drug release rate and toxicity of the nanoparticles were evaluated. FIGS. 8, 9 and 10 show the scanning electron microscope (SEM) images of nanocomposite particles obtained at various conditions. Most of the particles were spherical in shape, with a similar size distribution. A few larger particles were present, which could be removed by a secondary filtration step, if desired.

Figure 11:
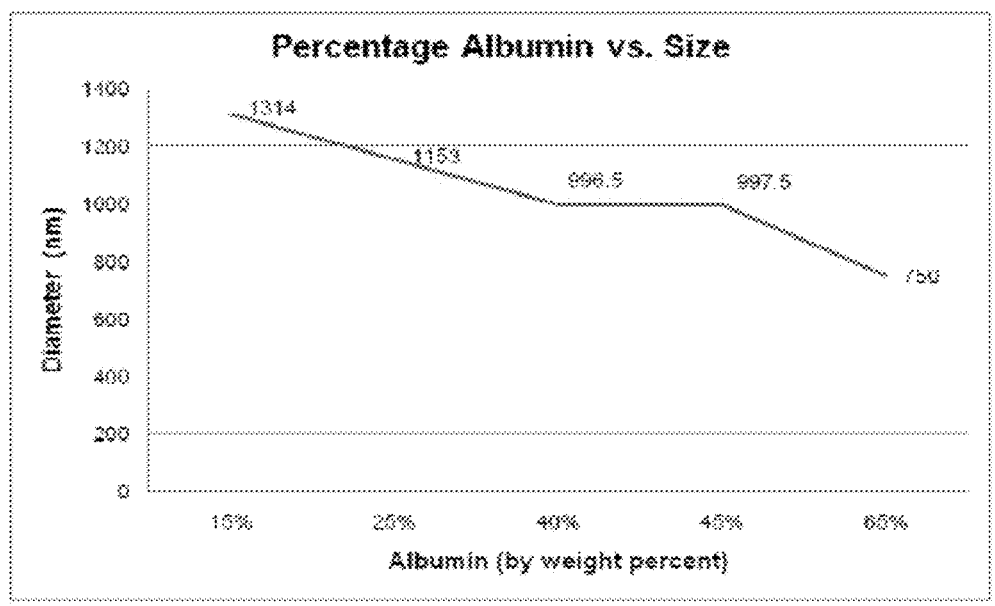
FIG. 11 is a graphic representation of the relationship between final diameter of composite spheres and the weight percentage of albumin contained in the spheres.

FIG. 11 is a plot of the diameters of nanocomposite particles as a function of albumin loading. In this study, the particle sizes were analyzed using a zetasizer for each sample set. The size of the nanocomposite particles tended to decrease as the percentage of albumin was increased. For example, at 15, 25, 40 and 65 wt % of albumin present in the particles, the average particle diameters were 1314, 1153, 996.5 and 750 nm, respectively. It is postulated that, at higher concentration, the viscosity of the solution was significantly reduced, resulting in production of smaller nanocomposite spheres.

Cytotoxicity

The effect of the drug delivery system on living cells was studied in vitro by growing cells in an incubator at 37° C. in a 96 well plate at a concentration of 5000 cells/well/100 µl. This was done in accordance with a study by Zilberman et. al., where microspheres loaded with horseradish peroxidase were studied for its effect of copolymer composition on microstructure and release profile. A serial dilution of MTX was prepared and added to the wells, then the plates were incubated for 3 and 5 days. Prior to reading, 20 µl of MTT (5 mg/ml) was added to the cells and then the plates were allowed to incubate for 6 hours. Next, the medium was changed to 200 µl of 10% SDS. After 150 µl of solution had been transferred to a new plate, the plate was read using OD 590. According to the Beer-Lambert law, the absorbance of light through a liquid is related to the material properties of the liquid. The concentration of MTT is measured by the difference in the absorbance of the liquids in the different cells in the plate.

Figure 12:
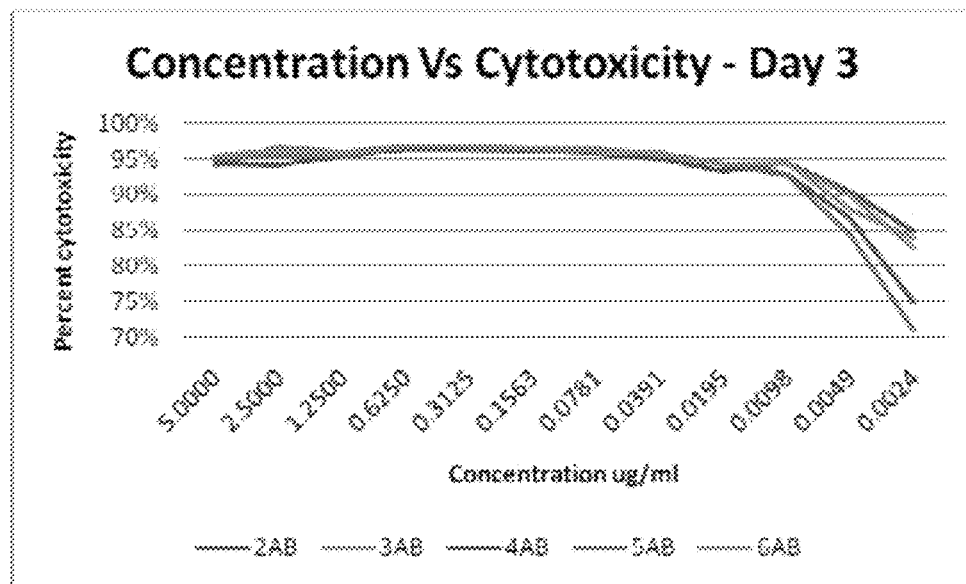
FIG. 12 is a graphic representation of readings after 3 days' exposure to a drug delivery system.
Figure 13:
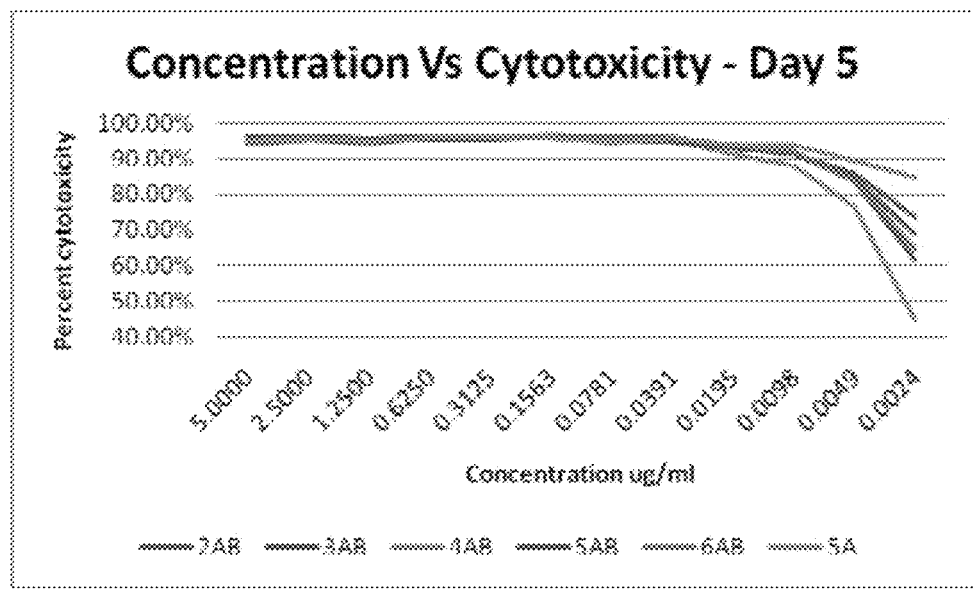
FIG. 13 is a is a graphic representation of readings after 5 days' exposure to a drug delivery system.

The cytotoxicity of the nanocomposite particles at days 3 and 5 is shown in FIGS. 12 and 13. Cells grown in medium without the drug delivery system remained healthy. When 100 µg to 1 µg of the drug delivery spheres were administered, most of the cells died. This effect may be attributed to the toxicity of the MTX drug. Only when less than 1 µg of particles were administered to the cells was there a noticeable difference in toxicity. Cytotoxicity of the drug carrying system is shown in FIGS. 12 and 13 to be high at the beginning of the release profile. As the concentration decreases, the cytotoxicity decreases for all of the batches.

Release Rates

For long term treatment of RA, the polymer must exhibit slow rates of diffusion, degradation and swelling in order to release a constant level of therapeutic agent into the affected area. Different variables such as choice of polymer, copolymer ratios, molecular weight, solution viscosity, surfactants, hydrophobic interactions, encapsulated materials, solvent, solvent evaporation rates, mixing speeds, mixing blades and generated heat will affect the particle size and therapeutic agent release rate. Earlier studies have shown that polymer microparticles can provide a steady release of the therapeutic agent for weeks. There are known to be at least two bursts (periods during which the therapeutic agent is released at an increased rate) when PLGA 50/50 is used. The first burst occurs within the first 24 hours, and the second burst occurs after 10 to 12 weeks.

A magnetic targeting component is used in this study for direction of the drug delivery system to the preselected target area as quickly as possible, so that the initial drug release burst will occur as close to the affected tissues as possible. The nanocomposite particles used in this study fully degrade in less than 10 weeks, which foreclosed the second burst phenomenon. The rate at which the composite nanoparticles broke down in a liquid medium was determined by measuring the amount of protein released from the nanoparticles to the medium at set intervals. In order to do this, a quantity of the nanoparticles was added to phosphate-buffered saline (PBS) to yield a concentration of 10 mg/ml. 200 µl of this mixture was placed in a tube and incubated at 37° C. for a prescribed number of days. Following the timed incubation, the tubes were centrifuged and the color of the supernatant was analyzed using a plate reader reading at OD 562.

Figure 14:
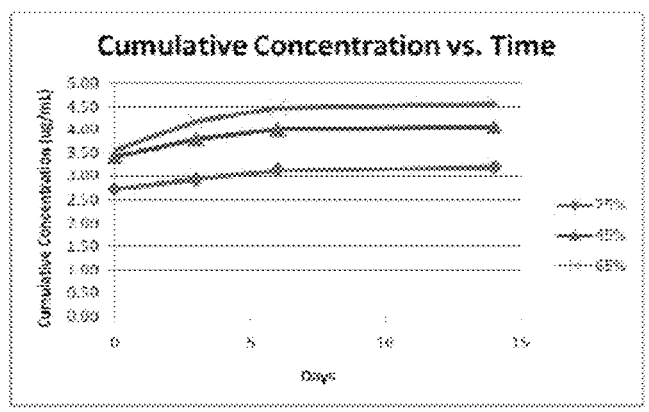
FIG. 14 is a graphic representation of the cumulative concentration of protein detected over time in a liquid medium containing batches of composite spheres with different percentages of albumin.

FIG. 14 shows the cumulative concentration of protein detected in a liquid medium as a function of time. All of the batches exhibited a similar release profile and, regardless of batch composition, all of the protein was released from the particles by the end of the first week. The cumulative concentration of protein that was detected corresponded directly to the percentage of albumin initially contained in the spheres. The albumin enriched spheres demonstrated higher release kinetics.

Conclusions

In this study, a polymeric drug delivery system having both a magnetic and a biological based targeting mechanism was designed, fabricated and tested in vitro. Tests showed the delivery system released the therapeutic agent in a controlled manner. All components of the system (excluding the drug) were biocompatible, non-toxic and non-immunogenic. The drug selected was FDA-approved and suitable for long term use. The preliminary results were positive, preparing the way for future in vivo testing.

In use, it is anticipated that the targeted drug delivery system described in this experiment would be used in a first targeting phase that employs an externally applied magnetic field to draw the system to the affected area. A second phase would utilize an internal targeting component to draw the spheres into the synovial membrane of only those areas affected by RA. The breakdown of the polymer would provide a timed release mechanism for controlled delivery of the therapeutic agent to the joints.

Example III

Figure 15:
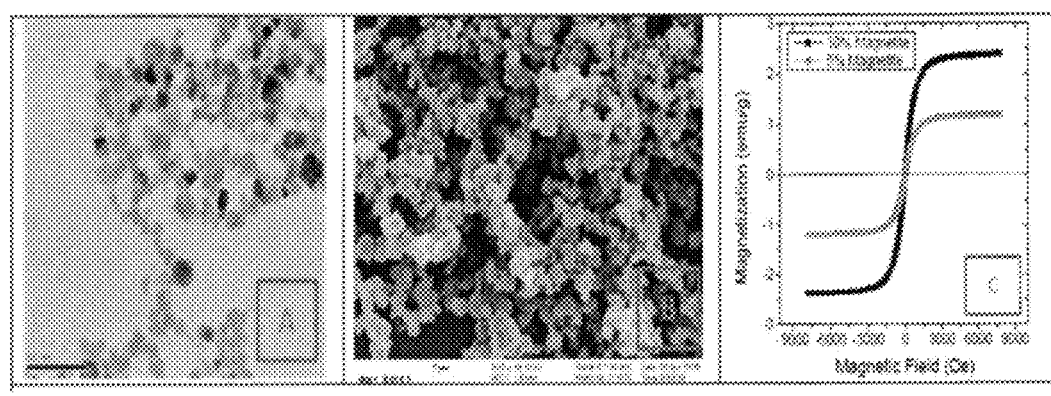
FIG. 15 left Panel is a TEM image showing size and shapes of magnetite nanoparticles, with a bar at 50 nm; center Panel is a SEM image of drug-carrying nanocomposite spheres with magnetite nanoparticles, albumin and drug in a PLGA matrix, with a bar at 2 pm; right Panel is a graphic representation of BSM data of Superparamagnetic nanocomposite spheres obtained at RT.

This study involves fabrication of biodegradable nanocomposite particles for drug delivery purposes. The particles were then characterized to determine their size distribution, morphology and magnetic properties using to determine their size distribution, morphology, and magnetic properties using scanning electron microscopy (SEM), transmission electron microscopy (TEM), dynamic laser light scattering (DLLS), and a vibrating sample magnetometer (VSM).
Materials and Methods Poly(lactic-co-glycolic acid) (PLGA) was embedded with magnetic nanoparticles (MNPs), human serum albumin and Methotrexate (MTX) using the oil-in-oil emulsion/solvent evaporation technique described in Example I. Magnetite nanoparticles with an average diameter of 10 nm as shown in FIG. 15 (left Panel) were prepared using a chemical co-precipitation technique where MNP and MTX concentrations in PLGA were 5%. Six samples (1AB, 2AB, 3AB, 4AB, 5AB and 6AB) with different albumin and PLGA contents were prepared to determine their properties. TABLE 2 shows the formulation of magnetic nanocomposite spheres.

SEM was used to characterize the samples prepared at each concentration. FIG. 15 (center Panel) shows the SEM image of Sample 2AB containing 5% MIX, 5% Magnetite, 15% Albumin and 75% PLGA in the spheres. The nanocomposite particles have a diameter between 200 nm and 1.1 µm, which also confirms DLLS test results. The VSM technique was used to characterize the magnetic properties of biodegradable nanocomposite spheres. For each sample, the magnetization at room temperature was measured over a range of applied fields between −8,000 and +8,000 Gauss. The plot of FIG. 15 (right Panel) shows that, near about 5,000 Gauss, the magnetization reaches a saturation value roughly proportional to the magnetite nanoparticle contents (5% and 10%) in these samples.
Results

TABLE 2

Formulation of Nanocomposite Samples for RA Drug Delivery System

| BATCH | MTX (%) | Magnetite (%) | Albumin (%) | PLGA (%) |
|---|---|---|---|---|
| 1AB | 5 | 5 | 5 | 85 |
| 2AB | 5 | 5 | 15 | 75 |
| 3AB | 5 | 5 | 25 | 65 |
| 4AB | 5 | 5 | 40 | 50 |
| 5AB | 5 | 5 | 45 | 45 |
| 6AB | 5 | 5 | 65 | 25 |

Example IV

Figure 16:
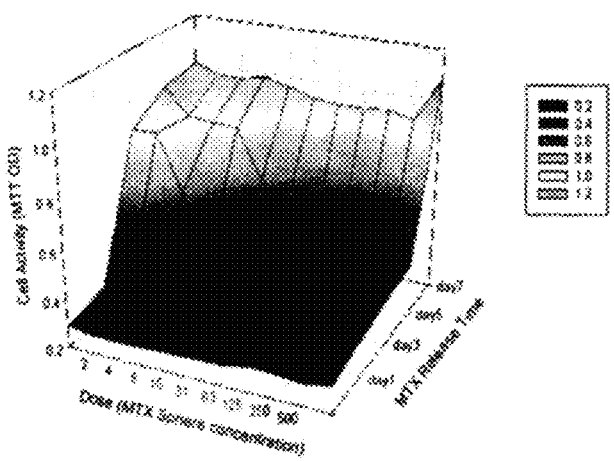
FIG. 16 is a three dimensional graphic representation showing cell viability following exposure to MTX nanocomposite spheres.
Figure 17:
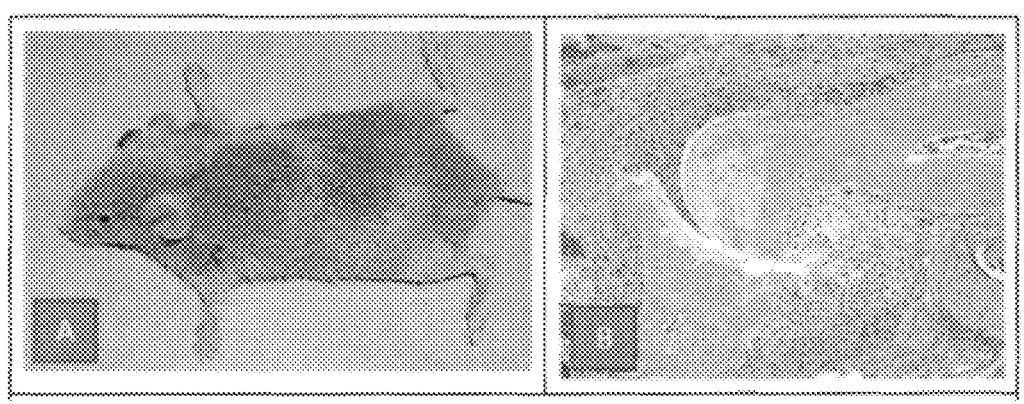
FIG. 17 is a photographic representation of the macroscopic (left Panel) and pathological appearance (right Panel) of murine collagen-induced arthritis in a mouse.

This study involved assessment of cell viability following exposure to MTX-carrying nanocomposite spheres.
Materials and Methods MTX was added to a 20% final concentration with 39% PLGA, 39% albumin, 1% Fe3O4, and 1% 1,6-Diphenyl-1,3,5-hexatriene (DPH) to fabricate the nanocomposite particles. The nanoparticle sample was sonicated and filtered using a 200 nm PTF filter. To assay for MTX release from the particle preparation, 10 mg of nanoparticles was added into 1 ml of medium, incubated at 37° C. overnight and the supernatant harvested (1 ml) to determine Day1 MTX release. Fresh medium (1 ml) was added to replenish the culture and incubation was continued for two more days, and the harvest and replenish cycle was repeated to obtain drug release media at 1, 3, 5, and 7 days. The 3T3 cell line was seeded in tissue culture plates at a concentration of $2 \times 10^5$ per well, and MTX supernatant added after 24 hours of culture. The particle concentration was titered from 1000 µg/100 µl/well to 2 µg/10 µl/well, and tissue culture was continued for 6 days. MIT (5 mg/ml) was added to each well for 6 hours, and the cells were then solubilized using 200 µl of 10% SDS at 37° C. overnight. 150 µl of supernatant was transferred to an assay plate, and the optical density was read at 590 nm. The data was analyzed to determine drug release from the nanoparticles over time in proportion to particle concentration.
Results The results are shown in FIG. 16, which demonstrates sustained release of MTX at physiological nanoparticle doses.

Example V

Type II collagen-induced arthritis (CIA) in mice is an experimental model with a number of pathological, immunological and genetic features in common with rheumatoid arthritis. This disease is induced by immunization of susceptible strains of mice with type II collagen, the major component of joint cartilage. A progressive, inflammatory arthritis develops in the majority of immunized animals, which is characterized clinically by erythema and edema, with affected paw typical width increases of 100%. A clinical scoring index has been developed to assess disease progression to joint distortion and spondylitis Histopathology of affected joints reveals synovitis, pannus formation, and cartilage and bone erosion, which may also be represented by an index. CIA provides a model to examine the influence of modified antigen presentation on the influence of modified antigen presentation on the autoimmune response, including the use of i.v. antigens, oral tolerance and passive antibody transfer.
Materials and Methods In this study, a fluorescent 1,6-Diphenyl-1,3,5-hexatriene (DPH) labeling material was also encapsulated into the drug delivery system associated with fluorouracil (5-FU), PLGA, albumin, and magnetite nanoparticles, and the locations of the drug release were marked by fluorescence exposure.
Results Comparing the tissue specimens under a fluorescence microscope with the H&E stained sections clearly showed that the fluorescence signals were sporadically penetrated into the skin tumor tissue and particularly condensed in many keratin-rich areas within the tumor tissue, which suggests that the DPH was a concentrated tumor site. FIG. 4A shows fluorescence in the darker areas of FIG. 4B. FIG. 4C is an enlarged section of FIG. 4D. Fluorescence-concentrated areas appear to be correlated with the keratin-like areas. The cells in the areas exhibited cell membrane disruption and nuclear disappearance, and cell debris were ubiquitous. The drug 5-FU has been a chemo-agent for squamous cell carcinoma (SCC). Thus, the evidence of both fluorescence and the presence of dying cells suggest that the carrier system is infiltrating into the center of the tumor. These data using a tumor model suggest that nanoparticle location and drug delivery may be readily accomplished in murine tissue, and support the concept of location of MTX loaded nanoparticles within the peripheral limbs of arthritic mice.

Example VI

Several nanocomposite spheres are fabricated, tested and evaluated for performance in treatment of an experimental arthritis model.
Materials and Methods
Biodegradable polymeric materials, including poly(lactide-co-glycolide) and chitosan, are utilized after dissolving in appropriate solvents (e.g., acetonitrile, dichloromethane, ethanol, etc.) substantially as described in Example I. Prior to the synthesizing process, it is ensured that different magnetic nanoparticles (magnetite and cobalt ferrite) are well dispersed in these polymeric materials.
Characterization
The physical properties of the nanocomposite particles are determined by SEM, TEM, vibrating sample magnetometer (VSM), atomic force microscopy (AFM), differential scanning calorimeter (DSC), thermogravimetric analysis (TGA), X-ray diffraction (XRD), X-ray photoelectron spectroscopy (XPS), UV visible (UV-Vis) spectroscopy, and Fourier transform infrared spectroscopy (FTIR). These tests enable determination of the degree of dispersion, size and shape, interfacial interaction, elemental distributions, crystallinity, surface contamination and surface morphology at micro and nanoscales. Sphere degradation, drug release rates, magnetic nanoparticle agglomeration and cytotoxicity are also determined.
Localized Arthritis Therapy Using a Magnetic Field
The therapeutic influence of the magnetic spheres associated with the RA drug are evaluated using in vivo tests under different magnetic fields. FIGS. 18B and 18C depict the schematic localizations of nanocomposite spheres with and without magnetic fields. Permanent magnets are closely placed around the arthritic joints to increase the concentration of drug carrying magnetic spheres, as shown in FIG. 18C. Incorporation of albumin into the nanocomposite spheres further increases the interaction between inflamed tissue and drug molecules and reduces the amount of magnetic field and magnetic nanoparticles.
Fifty DBA/1 LacJ mice (9 weeks of age) are randomly divided into 5 groups and immunized intradermally with 100 pg of bovine collagen II in complete Freund's adjuvant (CFA) to induce arthritis. On the day of arthritis onset, the mice receive an iv injection of: (1) 200 µl of sterile saline (control), (2) 200 µl of sterile saline containing $10^5$ nanoparticles loaded with MTX, (3) 200 µl of sterile saline containing $10^4$ nanoparticles loaded with MTX, (4) 200 µl sterile saline containing $10^5$ unloaded nanoparticles, and (5) 200 µl sterile saline containing MTX alone. One arthritic limb is inserted into a permanent 'pot' magnet and secured using a custom harness that allows the mouse to ambulate. The magnet is removed after four hours, and the arthritic animals are clinically assessed five times per week and paw measurements will be recorded three times a week for 3 weeks after the therapy. The peripheral joint bone density of all mice is scanned and recorded by microCT pre-arthritis, and every 7 days following onset and treatment. Mice are sacrificed at 3 weeks post therapy and arthritic paws assessed for pathological changes, including the presence of synovitis, pannus formation, marginal erosions, architectural changes (mostly subluxation), and destruction. An overall score, based on these collective points, is assigned to each section. This study provides an indication of anti-arthritic and anti-inflammatory activity of MTX nanoparticle therapy in the experimental murine model of arthritis, and indicate gross changes in joint/bone structure due to the treatment.

Example VII

Figure 22:
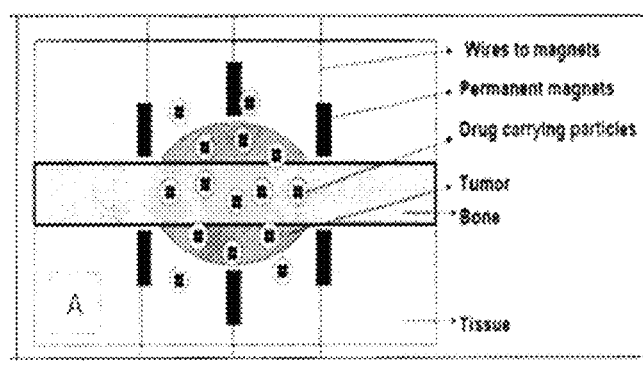
FIG. 22 is a schematic illustration of magnetically targeted drug delivery for a bone cancer treatment.

Materials and Methods, Characterization
Drug-carrying magnetic nanocomposite particles are prepared as described in Example VI, except that known amounts of bone cancer drugs, including MTX, 5-FU or cisplatin are separately added to the PLGA/albumin solution rather than MTX. FIG. 18A shows a schematic illustration of the magnetic nanocomposite sphere fabrication. The particles are characterized as described in Example VI.
Localized Bone Cancer Therapy Under Magnetic Field
The therapeutic influence of the magnetic particles associated with the anti-cancer drug are evaluated using ex vivo and in vivo tests. Small permanent magnets are surgically placed near the tumor sides in the mouse model of osteosarcoma in order to increase the drug-carrying nanocomposite sphere concentrations around the tumor. FIG. 22 shows the magnetically targeted drug delivery for a bone cancer treatment using permanent magnets.
Human osteosarcoma cells (ATCC collection) are propagated in culture. Four-week-old nude mice are used to establish the orthotopic osteosarcoma model. Mice are divided into four groups. Under strict sterile conditions, surgical exposure of the proximal end of the tibia followed by drilling a small hole across the metaphysis with a 0.8 mm dental drill is performed. Two groups of mice have four small magnet bars (generating 0.1-1 T in local tissue) placed subcutaneously around the hole before suturing the skin together. The third and fourth groups of mice receive the sham operation only without magnet bar implantation. Through that restricted entry site, 40 µl of culture medium containing 105 osteosarcoma cells is injected into the transmetaphysial hole immediately after surgery. At 21 days after surgery, when microCT confirms tumor growth in the tibia, mice in group 1 (magnet bar implanted) and group 3 (no magnet) begin treatment by pen-tumor injections, at two-day intervals, of 50 µl of magnetic nanoparticles (between 200 nm and 2 µm) loaded with the anti-cancer drug. The mice continue to be housed in sterile micro-isolator cages, with normal diets and water. The growth and metastatic progression of the tumors is monitored closely by macroscopic examination and periodic microCT evaluation. The mice are sacrificed after 4, 6, 8, and 12 weeks for histological, molecular, and biochemical analyses. Six mice per group per sacrifice point (determined by Power Analysis) are used for data reproducibility.
It is to be understood that, while certain forms of the magnetic nanoparticle drug delivery system have been illustrated and described herein, the invention is not to be limited to the specific forms or arrangement of elements described and shown.

We claim:
1. A method of localized therapy including the steps of: providing a quantity of composite nanoparticles comprising a synthetic resin polymer composition, magnetic nanoparticles, a biological targeting component that draws the composite nanoparticles into tissue, and a pharmaceutical composition, positioning magnets adjacent an area of a patient to be treated, delivering a quantity of the composite nanoparticles into the body of the patient, and magnetically drawing the composite nanoparticles to the affected area, wherein said biological targeting component that draws the composite nanoparticles into tissue is albumin.

2. The method of localized therapy of claim 1, wherein a quantity of $10^4$ to $10^5$ composite magnetic nanoparticles is delivered into the body of a patient by injection into the bloodstream.

3. The method of claim 1, wherein the amount of biological targeting component that draws the composite nanoparticles into tissue in the composite nanoparticles comprises from about 5% to about 85% (v/v).

4. The method of claim 3, wherein said synthetic resin polymer is biodegradable.

5. The method of claim 3, wherein said synthetic resin polymer is selected from the group consisting of poly(lactic-co-glycolic acid) or poly(D,L-lactide-co-glycolide) (or PLGA), chitosan, poly(lactic acid) (or PLA), poly(glycolic acid) (or PGA), polycaprolactone (or PCL), and combinations thereof.

6. The method of claim 5, wherein said synthetic resin polymer is PLGA.

7. The method of claim 6, wherein said PLGA is made up of monomers and each monomer is present in an amount ranging from 15% to about 85%.

8. The method of claim 1, wherein said composite nanoparticles include from about 5% to about 95% (w/v) of said synthetic resin polymer.

9. The method of claim 1, wherein said pharmaceutical composition is selected from the group consisting of antirheumatic agents (DMARDs), anti-inflammatory agents, anti-malarial medications, biological response modifiers, corticosteroids, cyclooxygenase-2 (COX-2) inhibitors, methotrexate, 5-Fluorouracil, doxorubicin, epirubicin, cyclophosphamide, docetaxel, doxorobicin, paclitaxel, cisplatin, and combinations thereof.

10. The method of claim 1, wherein said magnetic nanoparticle is selected from the group consisting of magnetite and cobalt ferrite.

11. The method of claim 1, wherein said composite magnetic nanoparticles include from about 0.5% to about 50% of said magnetic nanoparticles.

12. The method of claim 1, wherein said magnetic nanoparticles have a diameter of from about 5 nm to about 20 nm.

13. The method of claim 1, wherein said composite nanoparticle has an average diameter from about 40 nm to about 1.1 µm.

14. A method of localized therapy including the steps of: providing a quantity of composite nanoparticles comprising a biodegradable synthetic resin polymer composition selected from the group consisting of poly(lactic-co-glycolic acid) or poly(D,L-lactide-co-glycolide) (or PLGA), chitosan, poly(lactic acid) (or PLA), poly(glycolic acid) (or PGA), polycaprolactone (or PCL), and combinations thereof, magnetic nanoparticles, a biological targeting component that draws the composite nanoparticles into tissue, and a pharmaceutical composition, positioning magnets adjacent an area of a patient to be treated, delivering a quantity of the composite nanoparticles into the body of the patient, and magnetically drawing the composite nanoparticles to the affected area, wherein said biological targeting component that draws the composite nanoparticles into tissue is albumin.

15. The method of claim 14, wherein the amount of albumin in the composite nanoparticles comprises from about 5% to about 85% (v/v).

16. The method of claim 14, wherein said biodegradable synthetic resin polymer is PLGA.

17. The method of claim 14, wherein said pharmaceutical composition is selected from the group consisting of antirheumatic agents (DMARDs), anti-inflammatory agents, anti-malarial medications, biological response modifiers, corticosteroids, cyclooxygenase-2 (COX-2) inhibitors, methotrexate, 5-Fluorouracil, doxorubicin, epirubicin, cyclophosphamide, docetaxel, doxorobicin, paclitaxel, cisplatin, and combinations thereof.

18. The method of claim 14, wherein said magnetic nanoparticle is selected from the group consisting of magnetite and cobalt ferrite.

19. The method of claim 14, wherein said composite magnetic nanoparticles include from about 0.5% to about 50% of said magnetic nanoparticles.

20. The method of claim 14, wherein said magnetic nanoparticles have a diameter of from about 5 nm to about 20 nm.

21. The method of claim 14, wherein said composite nanoparticle has an average diameter from about 40 nm to about 1.1 µm.

22. The method of claim 14, wherein a quantity of $10^4$ to $10^5$ composite magnetic nanoparticles is delivered into the body of a patient by injection into the bloodstream.

23. The method of claim 16, wherein said PLGA is made up of monomers and each monomer is present in an amount ranging from 15% to about 85%.

24. The method of claim 14, wherein said composite nanoparticles include from about 5% to about 95% (w/v) of said biodegradable synthetic resin polymer.

* * * * *